United States Patent
Faber et al.

(10) Patent No.: US 10,092,428 B2
(45) Date of Patent: Oct. 9, 2018

(54) LOW PROFILE PROSTHESIS DELIVERY DEVICE

(71) Applicant: Cook Medical Technologies LLC, Bloomington, IN (US)

(72) Inventors: Jacqui Faber, Queensland (AU); Muhammed Ahsan, West End (AU); Sean O'Brien, New South Wales (AU); Nhi Nguyen, Greenslopes (AU); Joshua Griffin, Greenslopes (AU)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/973,068

(22) Filed: Dec. 17, 2015

(65) Prior Publication Data
US 2016/0184118 A1    Jun. 30, 2016

Related U.S. Application Data (60) Provisional application No. 62/098,051, filed on Dec. 30, 2014.

(51) Int. Cl.
*A61F 2/95*    (2013.01)
*A61F 2/07*    (2013.01)
(Continued)

(52) U.S. Cl.
CPC .............. *A61F 2/95* (2013.01); *A61F 2/06* (2013.01); *A61F 2/07* (2013.01); *A61F 2/2439* (2013.01);
(Continued)

(58) Field of Classification Search
CPC .............. A61F 2/95; A61F 2002/9505; A61F 2002/9511; A61F 2002/9522
See application file for complete search history.

(56) References Cited

U.S. PATENT DOCUMENTS

| | | | |
|---|---|---|---|
| 5,456,713 A | 10/1995 | Chuter | |
| 5,554,183 A * | 9/1996 | Nazari | A61F 2/07 623/1.13 |

(Continued)

FOREIGN PATENT DOCUMENTS

| | | |
|---|---|---|
| CN | 2855366 Y | 1/2007 |
| EP | 2517671 A2 | 10/2012 |

(Continued)

OTHER PUBLICATIONS

European Search Report for corresponding EP 15275273.9 dated Jun. 2, 2016, 7 pages.

(Continued)

*Primary Examiner* — Diane Yabut
(74) *Attorney, Agent, or Firm* — Brinks Gilson & Lione (57) ABSTRACT

A delivery device system for delivering a low profile prosthesis and a method for releasably retaining a prosthesis on the device are described. The delivery device comprises a prosthesis disposed about the proximal end of the inner cannula. In a first configuration the prosthesis is releasably secured to the inner cannula in a radially inwardly contracted low profile delivery configuration and in a second configuration the prosthesis is at least partially radially outwardly deployed. First and second trigger wires extend longitudinally and circumferentially about the prosthesis in helical configurations. The first trigger wire is helically wound in a clockwise direction and the second trigger wire is helically wound in a counter-clockwise direction. When the first and second helical trigger wires are in a tensioned condition, the prosthesis is releasably secured to the inner cannula in a radially inwardly contracted low profile delivery configuration.

19 Claims, 6 Drawing Sheets

(51) Int. Cl.
*A61F 2/06* (2013.01)
*A61F 2/24* (2006.01)

(52) U.S. Cl.
CPC ... *A61F 2002/072* (2013.01); *A61F 2002/075* (2013.01); *A61F 2002/077* (2013.01); *A61F 2002/9505* (2013.01); *A61F 2002/9511* (2013.01); *A61F 2230/0013* (2013.01); *A61F 2230/0091* (2013.01)

(56) References Cited

U.S. PATENT DOCUMENTS

| | | | |
|---|---|---|---|
| 5,720,776 | A | 2/1998 | Chuter et al. |
| 5,779,732 | A | 7/1998 | Amundson |
| 6,350,278 | B1 | 2/2002 | Lenker et al. |
| 6,716,238 | B2 * | 4/2004 | Elliott ................ A61F 2/95 623/1.11 |
| 6,808,529 | B2 | 10/2004 | Fulkerson |
| 6,942,691 | B1 | 9/2005 | Chuter |
| 7,534,256 | B2 | 5/2009 | Cragg |
| 8,328,861 | B2 | 12/2012 | Martin et al. |
| 8,468,667 | B2 | 6/2013 | Straubinger et al. |
| 8,603,156 | B2 | 12/2013 | Hartley et al. |
| 8,740,964 | B2 | 6/2014 | Hartley |
| 8,864,808 | B2 | 10/2014 | Greenberg et al. |
| 8,876,879 | B2 | 11/2014 | Hartley et al. |
| 8,911,488 | B2 | 12/2014 | Hartley et al. |
| 9,060,853 | B2 | 6/2015 | Roeder et al. |
| 9,173,756 | B2 | 11/2015 | Hopkins et al. |
| 2005/0288764 | A1 * | 12/2005 | Snow ................ A61F 2/95 623/1.11 |
| 2006/0009833 | A1 | 1/2006 | Chobotov et al. |
| 2007/0043425 | A1 | 2/2007 | Hartley et al. |
| 2007/0043430 | A1 | 2/2007 | Stinson |
| 2008/0082159 | A1 | 4/2008 | Tseng et al. |
| 2008/0319526 | A1 * | 12/2008 | Hill ................ A61F 2/2418 623/1.12 |
| 2009/0099648 | A1 | 4/2009 | Yu |
| 2010/0324651 | A1 | 12/2010 | Holzer et al. |
| 2011/0144735 | A1 * | 6/2011 | Hartley ................ A61F 2/95 623/1.11 |
| 2012/0041534 | A1 | 2/2012 | Clerc et al. |
| 2013/0268048 | A1 * | 10/2013 | Watson ................ A61F 2/07 623/1.11 |
| 2014/0074218 | A1 | 3/2014 | Leopold et al. |
| 2014/0148895 | A1 | 5/2014 | King |

FOREIGN PATENT DOCUMENTS

| | | |
|---|---|---|
| EP | 2604232 A1 | 6/2013 |
| WO | WO 96/18361 A1 | 6/1996 |
| WO | WO 2008/097590 A1 | 8/2008 |

OTHER PUBLICATIONS

NewsRX article on "Cook Medical Technologies LLC; Patent Issued for Stent Graphs for the Thoracic Aorta", Journal of Engineering, Dec. 25, 2013, p. 10240, obtained from the Internet on Oct. 7, 2014 at: http://search.proquest.com/professional.printviewfile?accountid=157282, 5 pages.
Examination Report for corresponding EP 15275273.9 dated Aug. 7, 2017, 3 pages.

* cited by examiner

Fig. 6

LOW PROFILE PROSTHESIS DELIVERY DEVICE

CROSS REFERENCE TO RELATED APPLICATIONS

This application claims the benefit of U.S. Provisional Application No. 62/098,051 filed on Dec. 30, 2014, the entire contents of which are hereby incorporated by reference.

TECHNICAL FIELD

This disclosure relates endovascular treatments and procedures and, in particular, an endovascular prosthesis such as a stent graft assembly having a low delivery profile.

BACKGROUND

The functional vessels of human and animal bodies, such as blood vessels and ducts, occasionally weaken or even rupture. For example, the aortic wall can weaken, resulting in an aneurysm. Upon further exposure to hemodynamic forces, such an aneurysm can rupture.

One surgical intervention for weakened, aneurysmal, or ruptured vessels involves the use of a prosthetic device to provide some or all of the functionality of the original, healthy vessel, and/or preserve any remaining vascular integrity by supporting a length of the existing vessel wall that spans the site of vessel failure. For example, techniques have been developed for repairing aneurysms by intraluminally delivering an endovascular prosthesis to the aneurysm site through the use of a catheter-based delivery system. A prosthesis of this type may be used, for example, to treat aneurysms of the thoracic aorta, abdominal aorta, iliac arteries, or branch vessels, such as the renal arteries. This invention, however, is not so restricted and may be applied to prostheses for placement in any lumen of the human or animal body.

The endovascular grafts typically include a tube of biocompatible pliable material (e.g., expanded polytetrafluoroethylene (ePTFE), polyethylene terephthalate referred to by the brand name Dacron®, or woven polyester) in combination with a graft anchoring component, which operates to hold the tubular graft in its intended position within the aorta. Most commonly, the graft anchoring component is formed of one or more frames or stents that is moveable between a radially inwardly compressed delivery configuration and radially expandable deployed configuration to exert outwardly directing radial pressure against the surrounding blood vessel wall. The stent can be either attached to or incorporated into the body of the tubular graft and/or delivered separately from the graft and subsequently deployed within the graft, or both. Preferably, the graft and stent components are loaded onto a delivery device in a manner that minimizes the load volume and maintains a low delivery profile.

SUMMARY

A prosthesis delivery device having a reduced graft load volume and compact delivery profile is described. One or more helically wound wires retain the graft and/or stent components of a prosthesis in a radially inwardly compressed delivery configuration on the delivery device to maintain the low profile, thus simplifying access, navigation and deployment of the prosthesis, particularly in patients with smaller vascular systems including children and in certain Asian populations, while also reducing complications and risk to the patient.

In one example, a low profile prosthesis delivery device is described. The delivery device comprises an inner cannula having a proximal end and a distal end and a prosthesis formed of biocompatible graft material and having a proximal end and a distal end. The prosthesis is disposed about the proximal end of the inner cannula. The prosthesis comprises a first position in which the prosthesis is releasably secured to the inner cannula in a radially inwardly contracted low profile delivery configuration and a second position in which the prosthesis is at least partially radially outwardly deployed. A first trigger wire extends longitudinally and circumferentially about the prosthesis in a helical configuration from the proximal end to the distal end of the prosthesis. The first trigger wire has a tensioned condition and a relaxed condition. A second trigger wire extends longitudinally and circumferentially about the prosthesis in a helical configuration from the proximal end to the distal end of the prosthesis. The second trigger wire comprises a tensioned condition and a relaxed condition. When the first and second helical trigger wires are in the tensioned condition, the prosthesis is releasably secured to the inner cannula in a radially inwardly contracted low profile delivery configuration.

A method for releasably retaining a prosthesis to a delivery cannula also is provided. The delivery cannula has a proximal end and a distal end and a prosthesis is releasably secured to the proximal end of the inner cannula. The prosthesis comprises a biocompatible graft material having a proximal end and a distal end. The prosthesis has a first position in which the prosthesis is releasably secured to the inner cannula in a radially inwardly contracted low profile delivery configuration and a second position in which the prosthesis is at least partially radially outwardly deployed. In one example, the method comprises extending a first trigger wire longitudinally and circumferentially about the prosthesis in a helical configuration from the proximal end to the distal end of the prosthesis, wherein the first trigger comprises a tensioned condition and a relaxed condition. The method further comprises extending a second trigger wire longitudinally and circumferentially about the prosthesis in a helical configuration from the proximal end to the distal end of the prosthesis, wherein the second trigger wire comprises a tensioned condition and a relaxed condition. The method further comprises tensioning the first and second helical trigger wires to releasably secure the prosthesis to the inner cannula in a radially inwardly contracted low profile delivery configuration.

DETAILED DESCRIPTION

The present disclosure relates to a system for implanting a radially expandable prosthesis within a human or animal body for repair of damaged vessels, ducts, or other physiological pathways and systems. In the present disclosure, the term "proximal" refers to a direction that is away from a physician during a medical procedure, while the term "distal" refers to a direction that is closest to the physician during the procedure.

Figure 1:
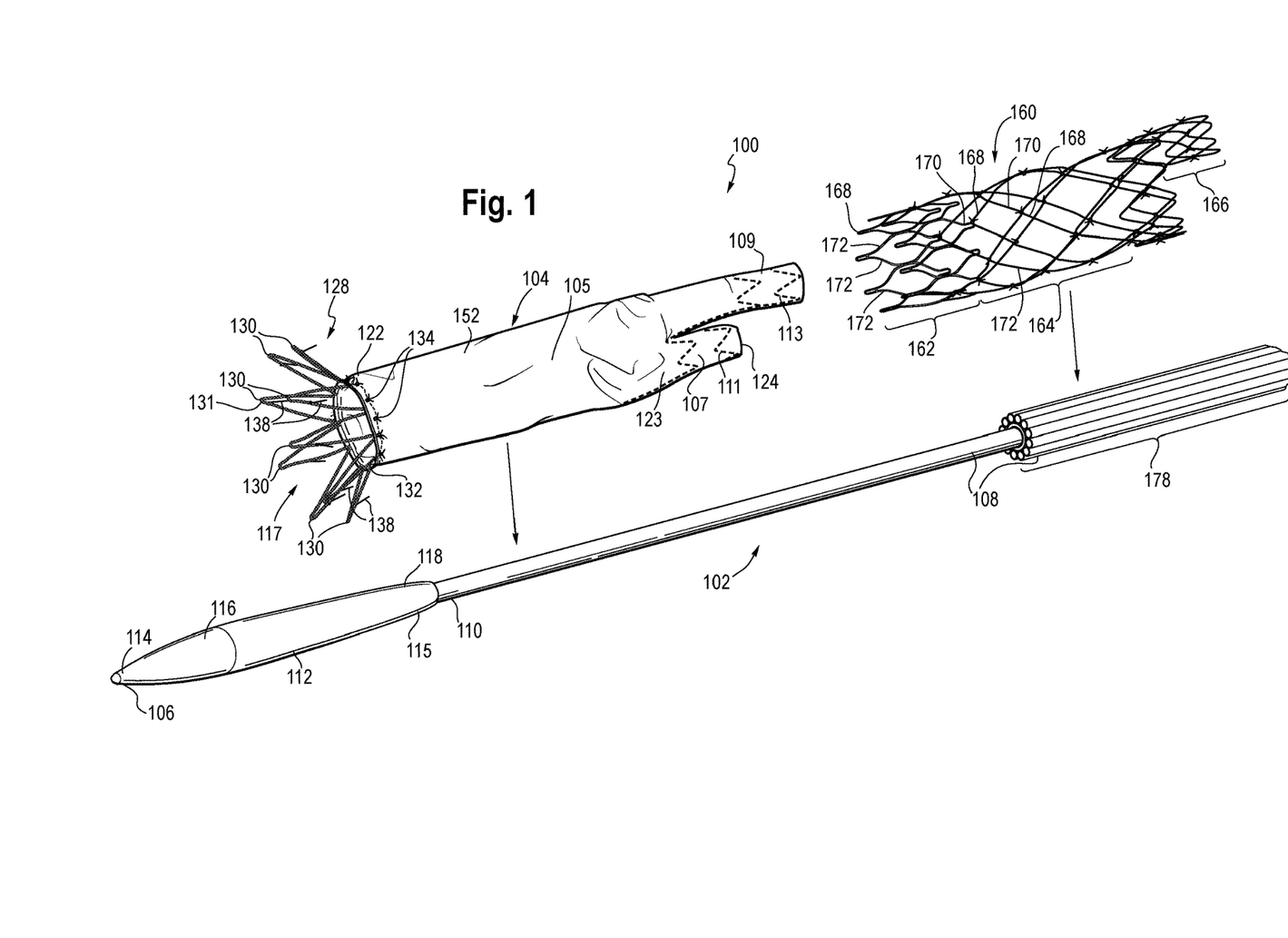
FIG. 1 is an exploded view of one example of a low profile prosthesis delivery device configured to releasably retain a prosthesis and stent subassembly thereon for delivery and deployment within a vessel.

FIG. 1 depicts an exemplary prosthesis 104. The prosthesis 104 may be positioned within a body vessel (not shown), such as a patient's aorta, to reinforce a weak spot or lesion in the body vessel at or near an aneurysm. In one example, the prosthesis 104 is positioned within the body vessel at or in the vicinity of a bifurcation, such as where the aorta meets the right and left common iliac arteries. Alternatively, the prosthesis 104 may be a generally tubular, non-bifurcated graft. The prosthesis 104 may provide strength to the injured or diseased body vessel at the aneurysm and may allow fluid to flow through the prosthesis 104 without further stress and/or trauma to the aneurysm, thus preventing enlargement and/or rupture of the body vessel at the lesion site. In a further example, the prosthesis 104 may be used for the treatment of a dissection.

As shown in FIG. 1, the prosthesis 104 comprises a bifurcated graft having any suitable length corresponding to a length of the lesion site at which the prosthesis is to be positioned. The main graft body 105 has a proximal end 122, a distal end 123 and first and second legs 107, 109, that extend from the distal end 123 of the main graft body 105. The first and second legs 107, 109, may be identical or they may differ. For example, the first and second legs 107, 109 may have the same length, or, as shown in FIG. 1, the first leg 107 and the second leg 109 may have different lengths. Further, the first leg 107 and the second leg 109 may have the same or differing widths, may be symmetrical or asymmetrical, or may comprise the same or differing materials. The main graft body 105, the first leg 107 and the second leg 109 may be constructed of any biocompatible graft material 152 which is suitable for facilitating repair of an injured or diseased body vessel. The graft material 152 may be synthetic and/or naturally-derived material. Synthetic biocompatible polymers may include polyethylene terephthalate, polyurethane, nylon, polyester, high molecular weight polyethylene, polytetrafluoroethylene, or combinations thereof. The graft material 152 should have sufficient flexibility to allow for delivery to a targeted area in the body. The graft material 152 can be porous or non-porous and also may be impregnated or coated with one or more therapeutic substances. In one example, the graft material 152 may be constructed of the commercially available material referred to as Dacron. The main graft body 105 may be constructed of the same material or of different material than the material of the first leg 107 and/or the second leg 109. Preferably, the graft material 152 is a low profile material or an ultra low profile material.

The prosthesis 104 may be anchored to an interior wall surface of a body vessel proximally and/or distally to a lesion site. For example, the proximal end 122 of the main graft body 105 may be anchored to a main vessel wall proximal to an aneurysm and the first and second legs 107, 109 may be anchored distal to the aneurysm, such as in one or more branch vessels.

Figure 2:
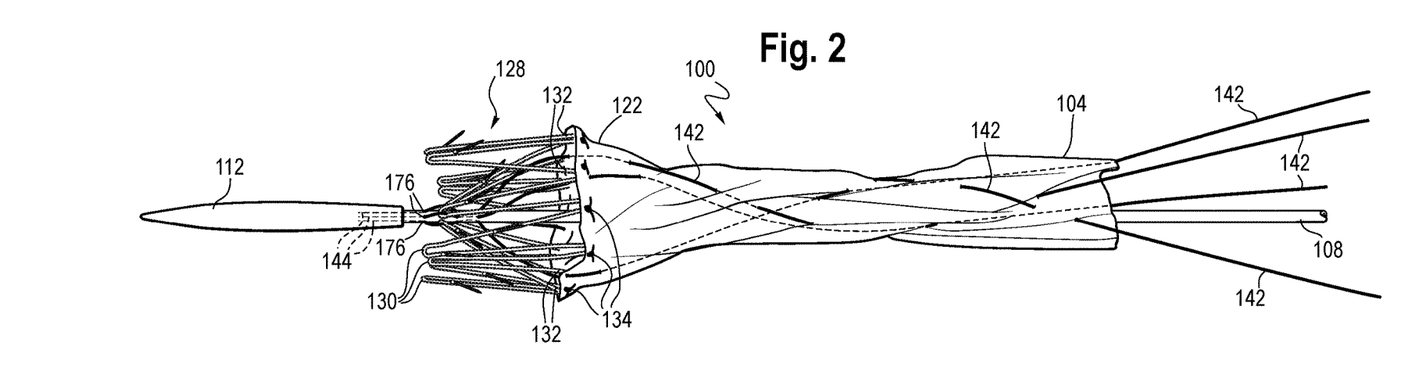
FIG. 2 shows one example of a prosthesis releasably retained on the proximal end of a prosthesis delivery device with helical trigger wires in a tensioned configuration.
Figure 3:
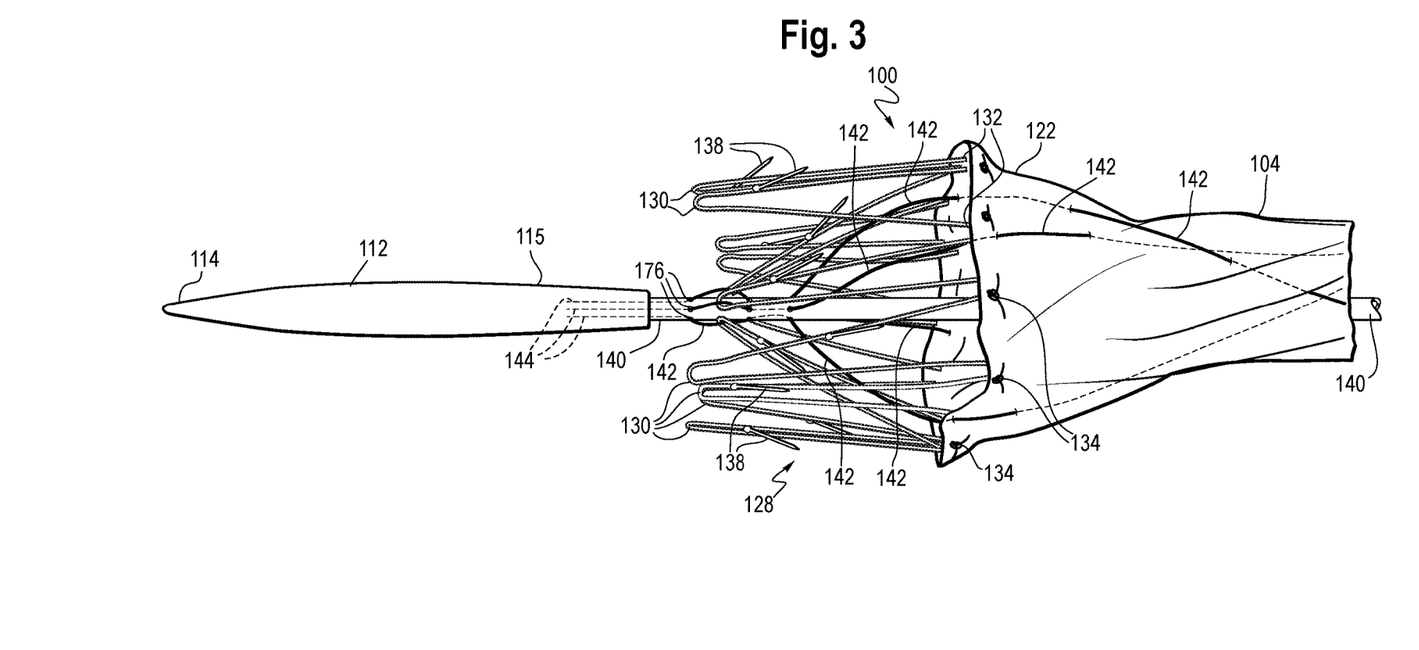
FIG. 3 shows an enlarged view of FIG. 2 showing one example of a proximal fixation stent at the proximal end of a prosthesis.

The proximal end 122 of the main graft body 105 may include an anchor. Suitable anchors include any means for attaching a prosthesis 104 to a body vessel wall. The anchor may be attached or adhered to the proximal end 122 of the main graft body 105 by any means, including but not limited to welding, stitching, bonding, and adhesives. As shown in FIGS. 1, 2 and 3, the anchor comprises a bare fixation stent 128. A fixation stent 128 may be attached to the proximal end 122 of the prosthesis 104. The fixation stent 128 has a proximal end with a series of proximal apices 130 and a distal end with a series of distal apices 132. In one example, fixation stent 128 is a z-stent with a series of proximal and distal apices 130, 132 such as six apices, eight apices, or ten apices at the proximal end and/or the distal end. In another example, the fixation stent 128 may be a twelve-apex stent. Another suitable stent is shown and described in U.S. Pat. No. 9,060,853 to Roeder et al. in FIGS. 1-15 and the accompanying text The distal end 132 of fixation stent 128 may be attached to the proximal end 122 of prosthesis 104 using any suitable mechanisms. In one example, one or more distal apices 132 of the bare fixation stent 128 is attached to the prosthesis 104 by a plurality of sutures 134. More particularly, the bare proximal fixation stent 128 may be attached to the proximal end 122 of the prosthesis 104 with a straight running stitch suture with Ethibond® over two double stitches of Prolene® 5.0. The bare proximal fixation stent 128 may be spaced from the proximal end 122 of the main graft body 105 such that the fixation stent 128 does not overlap the proximal end 122 of the main graft body 105. One or more sutures may serve to space the bare fixation stent 128 from the proximal end 122 of the main graft body 105, permitting a reduced delivery profile of the device 100. Alternatively, as illustrated in FIG. 1, the fixation stent 128 may be sutured directly to the proximal end 122 of the main graft body 105 so that there is at least some overlap with the proximal end 122 of the main graft body 105. The bare fixation stent 128 may comprise additional anchoring features, including but not limited to one or more anchoring barbs 138. Anchoring barbs 138 may be used to secure the prosthesis 104 within a vessel, duct, or lumen when deployed.

Further, as shown in FIG. 1, one or both of the first leg 107 and second leg 109 may include at least one stent 111, 113 located on the interior surface, exterior surface, or both internal and external surfaces of the graft material 152.

Alternatively, the first leg 107 and/or second leg 109 may be unsupported and therefore not include a stent. As FIG. 1 shows, the first leg 107 and the second leg 109 have differing lengths. A stent 111 is secured to the exterior surface at the distal end of the first leg 107 and another stent 113 is secured to the exterior surface at the distal end of the second leg 109. The first leg stent 111 and the second leg stent 113 are longitudinally staggered, such that the first leg stent 111 is proximal to the second leg stent 113 due to the differing lengths of the first and second leg 107, 109. In the event that the prosthesis 104 is not a bifurcated graft (e.g., the prosthesis is a generally singular tubular graft), then one or more stents may be located on the interior surface, exterior surface, or both of the graft material 152 at or near the distal end 123 of the main graft body 105. Alternatively, the prosthesis 104 may be unsupported along its length such that there are no body stents located on the graft material 152 between the proximal and distal ends 122, 124 of the prosthesis 104 other than the bare proximal fixation stent 128.

Suitable stents for use in connection with the prosthesis 104 described herein, including the proximal fixation stent 128, the first leg stent 111 and/or the second leg stent 113 may be self-expanding or mechanically-expandable stents or both, and may be deployed according to conventional methodology. For example, mechanically-expandable stents may be expanded by an inflatable balloon catheter, by a self-deployment mechanism (after release from a catheter), or by other appropriate means. In one example, one or more of the stents described herein may be commercially available from Cook Incorporated (Bloomington, Ind.). The stents may be made of one or more suitable biocompatible materials such as stainless steel, nickel-titanium alloy (nitinol), ceramic, cobalt/chromium alloys, aluminum or other biocompatible metals and/or composites or alloys such as carbon or carbon fiber.

As shown in FIG. 1, a stent subassembly 160 may be separately provided from the prosthesis 104. The stent subassembly 160 may comprise a single unitary stent or a series of stent segments. As shown in FIG. 1, the stent subassembly 160 comprises a series of stent segments secured together at multiple points to form the subassembly 160. Alternatively, one or more of the various stent segments may remain separate from each other (e.g., not secured by any attachment mechanisms).

In a non-limiting example, as illustrated in FIG. 1, the stent subassembly 160 may include a proximal sealing stent 162, one or more body stents 164 and one or more leg stents 166. The stent segments may be secured to each other by various mechanisms, including sutures, adhesives, welding and the like. As shown in FIG. 1, each stent segment has a series of proximal apices 168 and a series of distal apices 170 and a series of adjacent struts 172 extending between the proximal and distal apices 168, 170. One or more distal apices 170 of the proximal sealing stent 162 are secured to one or more proximal apices 168 of an adjacent, distally located body stent segment 164. The distal apices 170 of a body stent segment 164 are secured to one or more proximal apices 168 of an adjacent, distally located body stent segment 164. The distal apices 170 of a body stent segment 164 are then secured to one or more proximal apices 168 of an adjacent leg stent segment 166.

The proximal sealing stent 162, body stent(s) 164 and leg stent(s) 166 may have the same geometries or may have different geometries. As shown in FIG. 1, the proximal sealing stent 162 has a different geometry than the body stent(s) 164 and leg stents 166. The geometry of the proximal sealing stent 162 may help lock or secure the stent subassembly 160 to the graft material 152 of the prosthesis 104 when the stent subassembly 160 is deployed, as described in further detail below.

FIG. 1 shows the stent subassembly 160 separate from the prosthesis 104. The stent segments 162, 164, 166 that make up the stent subassembly 160 may be constructed of any suitable material that may be self-expandable, balloon-expandable, or a combination thereof, and in one example, the stent subassembly 160 may be self-expanding and made of nitinol. The stent subassembly 160 may be constructed of the same material as the bare proximal stent 128 and/or as the first or second leg stents 111, 113 or the stent subassembly 160 may be constructed of a different material.

The stent subassembly 160 may be delivered to a target location within a vessel and deployed separately from the prosthesis 104. In one example, prosthesis 104 may be delivered to a target location and deployed within a vessel. Next, the stent subassembly 160 may be positioned within a portion of the lumen 117 of the prosthesis 104 and deployed therein. In this example, the outer surface of the stent subassembly 160 engages an inner surface of graft material 152 of the prosthesis 104, so as to apply sufficient outward radial force to support the prosthesis 104 in a radially outwardly expanded or deployed configuration, while urging the prosthesis into contact with a vessel wall.

The stent subassembly 160 described above in connection with FIG. 1 is for exemplary purposes and shall not be construed as limiting. The stent subassembly 160 may be constructed of any one or more of the above described stent segments and/or any other variously shaped stent segments that are arranged into various other desirable subassembly configurations or orientations. The size, shape and configuration of the stent subassembly 160 may selected depending on several factors, including the configuration and dimensions of the prosthesis 104 into which it is intended to be deployed. The shape and configuration of the stent subassembly 160 and/or of the prosthesis 104 may therefore accommodate varying vessel diameters, shapes and curvatures, as necessary or desired based on the procedure being performed and to allow the prosthesis 104 to conform to the anatomy of a vessel. FIG. 1 shows a perspective view of an exemplary delivery system 100 for delivering a prosthesis 104 and/or for delivering a stent subassembly 160 to a desired location within a vessel. The delivery system 100 comprises an introducer 102 having a proximal end 106 and a distal end (not shown). The introducer 102 has an inner cannula 108 extending therethrough. The inner cannula 108 has a proximal end 110, a distal end (not shown). The proximal end 110 of the inner cannula 108 may extend into an introducer tip or nose cone 112. The introducer tip 112 has a proximal end 114 and a distal end 115. The introducer tip 112 may be tapered and have a long forward taper 116 and a shorter reverse taper 118, such that the introducer tip 112 presents an atraumatic tip for navigation through the vasculature and the reverse taper 118 presents an atraumatic surface to prevent the introducer tip 112 from catching or snagging on the prosthesis 104 or other parts of the delivery system 100. The introducer tip 112 preferably comprises an outer diameter that is larger than the outer diameter of any prosthesis 104 and or stent subassembly 160 that is releasably secured to the introducer in a radially inwardly contracted low-profile delivery configuration to maximize successful navigation and access to a particular location within the vasculature.

The inner cannula 108 may be a single lumen cannula such that only one lumen extends between the proximal end 110 and the distal end (not shown). The single lumen is preferably sized and configured to allow a guide wire (not shown) as well as one or more trigger wires 142 to be extended therethrough. In one example, the inner diameter of the inner cannula 108 is greater than about 0.038 inches, or any other suitable dimension to accept a conventional guide wire (not shown).

Figure 6:
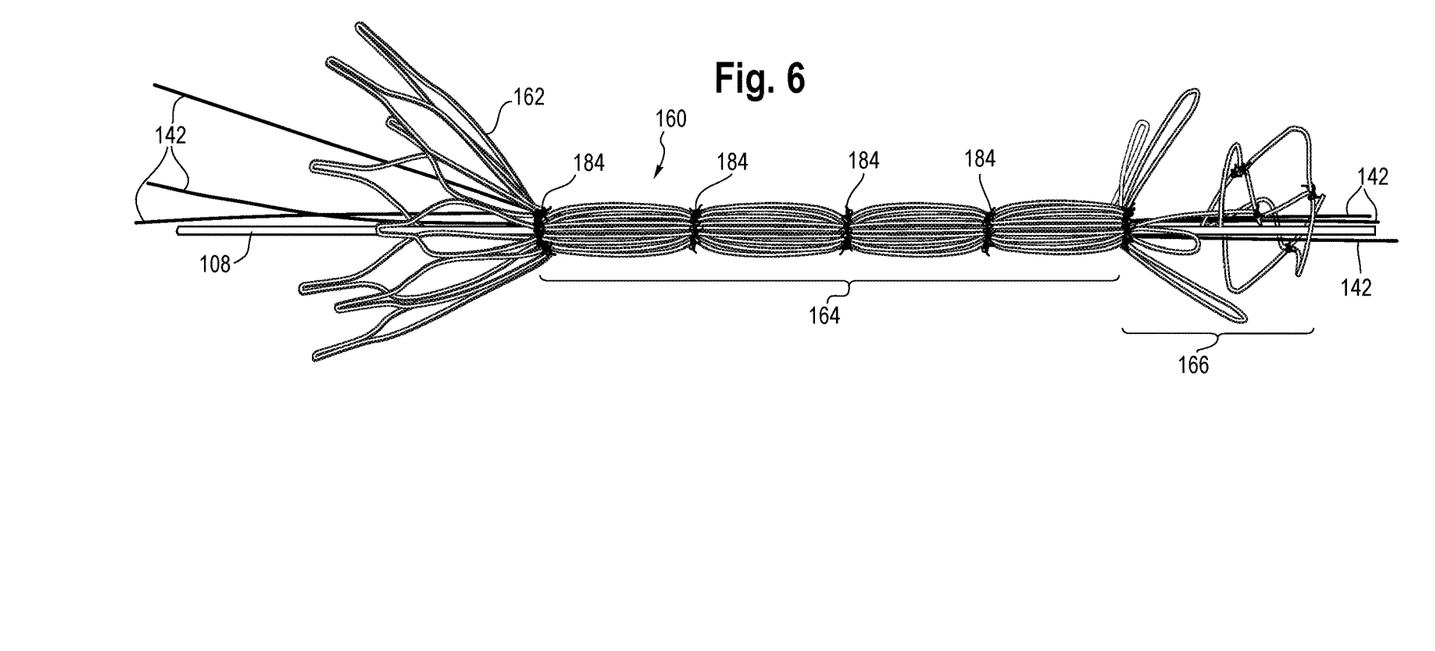
FIG. 6 is a longitudinal view of one example of a stent subassembly retained on a delivery device.
Figure 12:
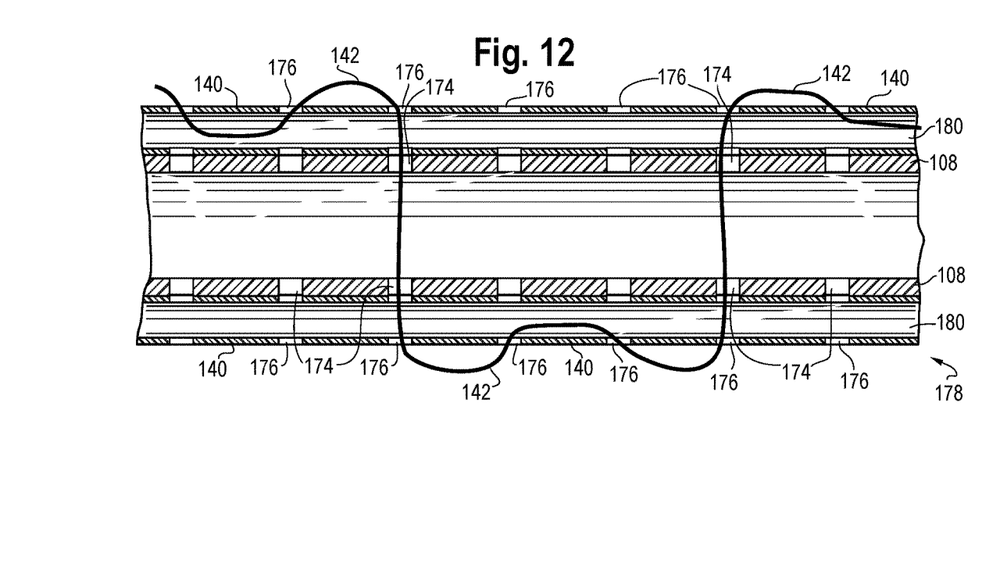
FIG. 12 is a longitudinal cross-sectional view of another example of an inner cannula and sleeve coaxial with the inner cannula and a trigger wire weaving in and out of the inner cannula and one or more apertures formed in the sleeve.

As shown in FIG. 12, the inner cannula 108 may comprise one or more holes or apertures 174 spaced longitudinally and/or spaced axially at pre-determined locations along the length of the inner cannula 108. One or more trigger wires 142 may be directed in and out of the inner cannula 108 via the holes 174 to radially capture the graft material 152 of the prosthesis 104 (and/or to radially capture one or more stent segments 162, 164, 166 of the stent subassembly 160 as shown in FIG. 6 (if the stent subassembly 160 is loaded onto the same introducer as the prosthesis) to provide effective axial fixation. More specifically, the element being retained and held in a reduced diameter delivery configuration on the inner cannula 108 (i.e., the prosthesis 104 and/or the stent subassembly 160) by the one or more trigger wires 142 may be prevented from moving or dislodging from the inner cannula 108 during delivery.

Figure 10:
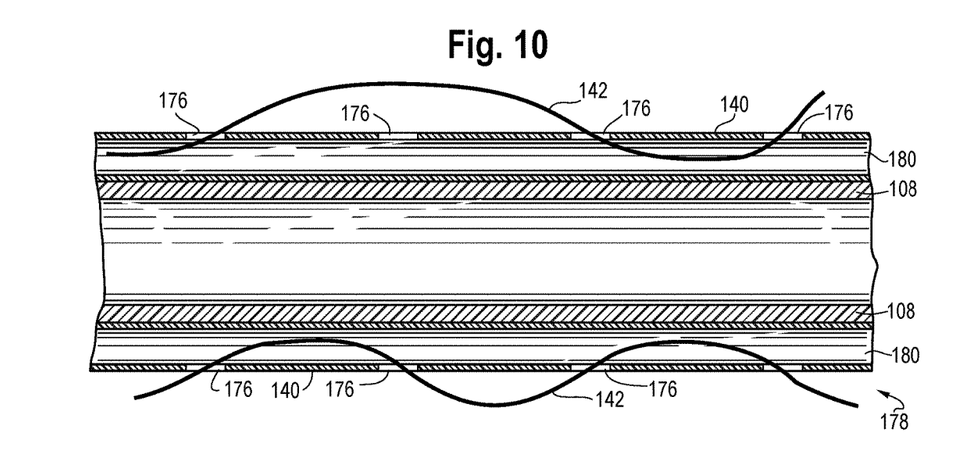
FIG. 10 is a longitudinal cross-sectional view of one example of an inner cannula and sleeve coaxial with the inner cannula and a trigger wire weaving in and out of one or more apertures formed in the sleeve.

A sleeve or sheath 140 may be coaxially disposed about and extend at least a portion of the longitudinal length of the inner cannula 108 and/or extend coaxially about at least a portion of the introducer tip 112. The sleeve 140 may be comprised of a flexible or pliable material such as rubbers, plastics, polymers, including but not limited to silicone or urethane. The sleeve 140 may be referred to as a UAT tube or "urethane attachment tube." The sleeve 140 may be used as a conduit through which trigger wires 142 may longitudinally extend. In particular, as shown in FIGS. 3, 10 and 12, the trigger wires 142 may extend between an outer surface of the inner cannula 108 and an inner surface of the sleeve 140. The sleeve 140 may retain the trigger wires 142, prevent them from entangling with each other or entangling with other portions of the device 100. As shown in FIGS. 10 and 12, the sleeve 140 may include one or more apertures 176 formed therein at pre-selected locations. A selected trigger 142 wire may extend out of one aperture 176 and then re-enter the sleeve 140 through another aperture 176. This allows the selected trigger wire(s) 142 to stitch or loop over a portion of a prosthesis 104 and/or over a portion of the proximal fixation stent 128 (and/or a portion of the stent subassembly 160) to secure the selected element to the inner cannula 108 as described in further detail below.

Figure 11:
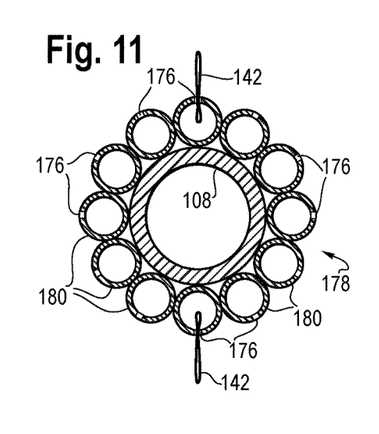
FIG. 11 is a cross-sectional view of the inner cannula and sleeve of FIG. 10.
Figure 13:
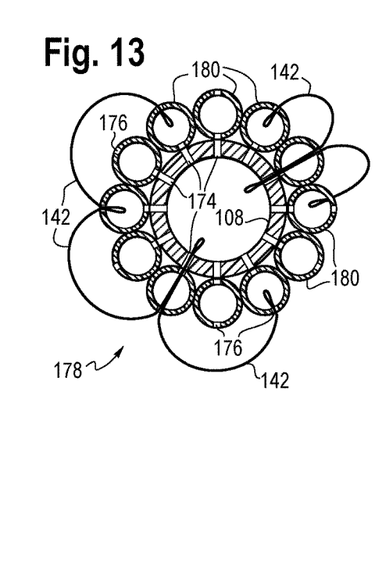
FIG. 13 is a cross-sectional view of the inner cannula and sleeve of FIG. 12.

Alternatively, the inner cannula 108 may be a multi-lumen cannula assembly 178 as shown in FIGS. 10-13. The multi-lumen cannula assembly 178 may be comprised of multiple smaller single lumen cannulas 180 arranged and/or attached together to form a unit having multiple lumens. Each of the smaller single lumen cannulas 180 may be arranged in a ring around a longitudinal axis, thus forming another inner or central lumen 108 running down the center of the ring along the length of the longitudinal axis. In a variation of this arrangement, multiple smaller single lumen cannulas 180 may be arranged around a centrally located single lumen cannula 108 as shown in FIGS. 11 and 13. The multiple smaller single lumen cannulas 180 may have an inner diameter that is only large enough to receive at least one trigger wire therethrough, such as 0.010 inches. The inner diameter of the multiple smaller single lumen cannulas 180 may have a greater diameter if necessary or desired. The inner diameter of the inner or central cannula 108 extending along the longitudinal axis formed by the ring of multiple smaller single lumen cannulas 180 may be similar to the single lumen cannula 108 described above, including but not limited to a central lumen greater than 0.038 inches, which is an accepted dimension to accept a conventional guide wire (not shown).

One or more of the multiple smaller single lumen cannulas 180 that form the multi-lumen cannula assembly 178 may include one or more holes or apertures 176 spaced longitudinally and/or spaced axially at pre-determined locations along the length of each of the multiple smaller single lumen cannulas 180. Also, as described above in connection with the single lumen cannula 108, a sleeve or sheath 140 may be coaxially disposed about and extend at least a portion of the longitudinal length of the multi-lumen cannula 178 and/or extend coaxially about at least a portion of the introducer tip 112. The sleeve 140 may include one or more apertures 176 formed therein at pre-selected locations that preferably correspond to and align with the apertures formed in the multi-lumen cannula assembly 178 as shown in FIGS. 10 and 12.

As shown in FIG. 12, a selected trigger wire 142 may extend out of one aperture 176 and then re-enter the sleeve 140 through another aperture 176 (and/or exit and re-enter the inner cannula 108 through one or more apertures 174). In this way, one or more trigger wires 142 could be directed in and out of one or more of the multiple smaller single lumen cannulas 180 (and/or the sleeve 140) via the apertures 174, 176 to radially capture the graft material 152 of the prosthesis 104 and/or one or to capture one or more stent segments 162, 164, 166 of the stent subassembly 160 (if the stent subassembly 160 is loaded onto the same introducer 102 as the prosthesis 104) to provide effective axial fixation. As shown in FIGS. 10-13, the one or more trigger wires 142 could loop in and out of the same smaller single lumen cannula 180 (FIG. 10 and FIG. 11) or may be woven between one or more different smaller single lumen cannulas 180 (FIG. 12 and FIG. 13). One of skill would recognize that the one or more trigger wires 142 can be woven in various differing weaving patterns in and out of the single lumen inner cannula 108 and/or the multi-lumen cannula assembly 178 to releasably retain the prosthesis 104 and/or the stent subassembly 160 to the inner cannula 108 during delivery.

As shown in FIG. 1, the inner cannula 108 may be a combination of a single lumen cannula and a multi-lumen cannula assembly 178. More specifically, the inner cannula 108 may be a single lumen cannula at a proximal end portion 106 of the introducer 102 and a multi-lumen cannula assembly 178 extending distally from the single lumen proximal end portion.

The prosthesis 104 and the stent subassembly 160 may be delivered and deployed within a vessel by any suitable introducer, including, but not limited to the introducer 102 described herein. In one non-limiting example, the prosthesis 104 and the stent subassembly 160 may be loaded onto separate sections of a single introducer 102 for delivery and sequential deployment. More specifically, the prosthesis 104 may be loaded onto a proximal end 106 of an introducer 102 and the stent subassembly 160 loaded onto the introducer 102 at a location distal to the prosthesis 104 so that there is no overlap between the respective components. For example, as shown in FIG. 1, the prosthesis 104 may be releasably attached to the single lumen portion of the inner cannula 108 and the stent subassembly 160 may releasably attached to the multi-lumen assembly portion 178 of the inner cannula 108. However, it is also contemplated that both the prosthesis 104 and the stent subassembly 160 may be releasably secured to an introducer 102 comprising only a single lumen inner cannula 108 or alternatively may be releasably secured to an introducer 102 comprising only a multi-lumen inner cannula assembly 178.

In one example, prosthesis 104 that is releasably secured to the inner cannula 108 may be a tubular graft, bifurcated graft, fenestrated graft or a combination thereof as necessary or desired depending on the procedure being performed and the portion of the vasculature being treated. The prosthesis 104 may be radially inwardly compressed on the inner cannula 108 to provide a low delivery profile, thereby facilitating transluminal delivery of the prosthesis 104 to the desired location within a vessel. The prosthesis 104 is also radially expandable during deployment as described below.

With the prosthesis 104 and stent subassembly 160 loaded on separate portions of a single introducer 102, the introducer may then be tracked to a desired location within a vessel. The prosthesis 104 may first be at least partially deployed and held in place in the vessel by the proximal fixation stent 128. The velocity of the flow of blood through the lumen 117 of the prosthesis 104 may serve to maintain the prosthesis 104 in at least a partially radially outwardly expanded condition. More specifically, the hemodynamic force or pressure created by the blood flowing through the vessel (and through the lumen 117 of the prosthesis 104) creates sufficient radial outward pressure against the walls of the prosthesis 104 so as to at least partially expand the prosthesis within the vessel. With the prosthesis 104 at least partially expanded, the introducer 102 may be further manipulated in order to position the stent subassembly 160 within the lumen 117 of the prosthesis. The stent subassembly 160 can then be deployed inside the lumen 117 of the prosthesis 104 to fully expand and deploy the stent subassembly 160 as well as the prosthesis 104.

Alternatively, the prosthesis 104 and the stent subassembly 160 may be loaded onto separate introducers and delivered separately to a desired location within a vessel. For example, the prosthesis 104 may be loaded onto a first introducer which is tracked to a location within a vessel where the prosthesis is at least partially deployed. The prosthesis 104 may be held in the vessel by the proximal fixation stent 128. As previously mentioned, the hemodynamic force created by the flow of blood through the lumen 117 of the prosthesis 104 may serve to maintain the prosthesis in at least a partially radially outwardly expanded condition, allowing a second introducer to be tracked to a desired location within the vessel. The second introducer, carrying the stent subassembly 160 in a radially inwardly contracted delivery configuration, may be tracked to a location that is at least partially within the lumen 117 of the prosthesis 104 and the stent subassembly 160 deployed therein.

Loading the prosthesis 104 and the stent subassembly 160 onto separate introducers or on separate portions of a single introducer 102 allows the overall delivery profile of the introducer 102 to be minimized. The prosthesis 104 and/or the stent subassembly 160 may be loaded onto an introducer 102 and held into a radially inwardly compressed delivery configuration by several diameter-reducing mechanisms.

The proximal end 131 of fixation stent 128 may be secured within a top cap and held by a trigger wire, as done with the Zenith® endovascular graft manufactured by Cook Medical of Bloomington, Ind. In another example, the bare fixation stent 128 may be releasably connected to the introducer tip 112. A recess formed in the inner surface of the introducer tip 112 may be configured to receive one or more proximal apices 130 of the bare proximal fixation stent 128 and retain it in a radially inwardly compressed delivery configuration. Alternatively or in combination, one or more of the proximal apices 130 of the bare proximal fixation stent 128 may be inserted into and secured within a portion of a sleeve (e.g., the UAT sleeve 140 shown in FIG. 3) that is disposed about the introducer tip 112 and/or disposed about the inner cannula 108 as further described below. In yet another example, alternatively or in combination with the above one or more trigger wires 142 may be utilized to releasably retain the proximal fixation stent 128 and/or the prosthesis 104 in a compressed delivery configuration on the introducer 102 while the same set of trigger wires 142 or a different set of trigger wires 142 may similarly be used to releasably retain the stent subassembly 160 in a compressed delivery configuration on the introducer 102 as shown in FIG. 6. For example, at least two trigger wires 142 may be used to releasably retain a proximal fixation stent 128 having six, eight or ten proximal apices 130 to the inner cannula 108. In another example, three or four trigger wires 142 may be used to releasably retain a proximal fixation stent 128 having ten or more proximal apices 130 to the inner cannula 108. In particular, four trigger wires 142 may be used to releasably retain a proximal fixation stent 128 having twelve proximal apices 130 to the inner cannula 108.

More particularly, as seen in FIGS. 2 and 3, delivery system 100 may include a diameter-reducing mechanism or arrangement consisting of one or more helical trigger wires 142 releasably connected to the introducer tip 112, fixation stent 128, and/or prosthesis 104, as described in greater detail below. If desired, the same set of helical trigger wires 142 may be used to releasably secure the stent subassembly 160 to the introducer 102 in a reduced diameter delivery configuration as generally shown in FIG. 6. Alternatively, a different set of trigger wires 142 or an entirely separate diameter-reducing mechanism altogether may be used to secure the stent subassembly 160 to the introducer 102 in a reduced diameter delivery configuration. For example, system 100 has two helical trigger wires 142. In another example, system 100 has four helical trigger wires 142. Any suitable number of helical trigger wires 142 may be used to releasably retain the prosthesis 104 and/or the stent subassembly 160 in a radially inwardly compressed delivery configuration on the introducer 102. Any suitable material can be used to construct helical trigger wires 142. In one example, helical trigger wires 142 are made of nitinol.

As shown in FIGS. 2-5, one or more of the helical trigger wires 142 may be wrapped, wound or coiled in a right-handed or clockwise direction about the prosthesis 104 while one or more of the other helical trigger wires 142 may be wrapped, wound or coiled in a left-handed or counter-clockwise direction about the prosthesis 104. For example, one helical trigger wire 142 is wound clockwise and another helical trigger wire 142 is wound counter-clockwise such that at least two trigger wires 142 are "counter-wrapped" about the prosthesis 104. As described below, helical trigger wires 142 may be positioned around and through the prosthesis 104 from the proximal end 122 to the distal end 124. The helical trigger wires 142 ensure the prosthesis 104 (and/or any stent sub-assemblies 160) are compressed and retained on the delivery device 100. When tension is applied to the one or more helical trigger wires 142, the diameter of the prosthesis 104 is reduced as the graft fabric 152 is captured down onto the inner cannula 108 as shown in FIG. 2.

As shown in FIGS. 2 and 3, the helical trigger wire 142 has a proximal end 144 and a distal end (not shown). The proximal end 144 of the helical trigger wire 142 can be releasably secured to the introducer 102. For example, as shown in FIG. 2, the proximal end 144 of the trigger wires 142 may be releasably retained on the introducer 102 by friction fit between an internal surface of the introducer tip 112 and an outer surface of the inner cannula 108. Alternatively, as shown in FIG. 3, the proximal end 144 of the helical trigger wires 142 may be inserted into and secured within a portion of the sleeve (e.g., the UAT sleeve 140) that is disposed about the introducer tip 112 and/or disposed about the inner cannula 108.

FIGS. 2 and 3 shows an example of how helical trigger wire(s) 142 releasably attaches to the introducer 100. The proximal end 144 of one or more of the helical trigger wire(s) 142 is secured within the sleeve 140 (or inner cannula 108) at the distal end 115 of the introducer tip 112. Each individual trigger wire 142 extends out of an aperture 176 formed in the sleeve 140 (or inner cannula 108) and loops over a proximal apex 130 of the bare fixation stent 128. The helical trigger wire 142 re-enters the sleeve 140 through another more distally located aperture 176 in the sleeve 140. Thus, the trigger wire 142 captures the proximal apex 130 of fixation stent 128 and secures it to the inner cannula 108. The helical trigger wire 142 then extends back out of the sleeve 140 (or, if the sleeve is not present, extends back out of an aperture formed directly in the inner cannula 108) through yet another aperture 176 formed in the sleeve 140 and loops over a distal apex 132 of the bare fixation stent 128 (the helical trigger wire 142 may also capture a portion of the graft material 152 at the proximal end 122 of the prosthesis 104 along with the distal apex 132 of the bare fixation stent 128). The helical trigger wire 142 extends further distally and helically wraps or spirals around the prosthesis 104, weaving in and out of the graft material 152 at selected points therealong as shown in FIGS. 2 and 3. The helical trigger wire 142 then exits the distal end 123 of the prosthesis 104 and extends distally along the length of the delivery system 100 to an external manipulation portion or handle of the device 100 (not shown). If the sleeve 140 is not present, then the one or more trigger wires 142 could weave in and out of apertures 174 formed directly in the inner cannula 108 (i.e., a single lumen inner cannula and/or a multi-lumen inner cannula assembly 178 depending on which one or both types of inner cannulas are being utilized) instead of a sleeve 140.

In another example, sutures (not shown) may be used to releasably secure the helical trigger wire(s) 142 to the prosthesis 104 instead of weaving the wire(s) 142 in and out of the graft material 152, thus avoiding having to pierce the graft material 152 with the helical trigger wire(s) 142.

Figure 4:
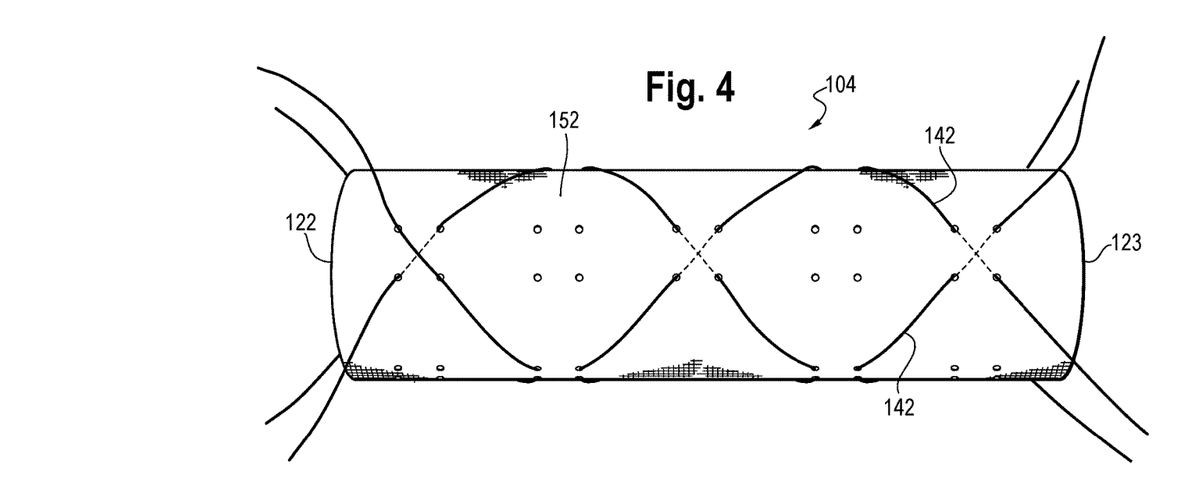
FIG. 4 shows a longitudinal view of one example of a prosthesis with the helical trigger wires in a relaxed configuration.
Figure 5:
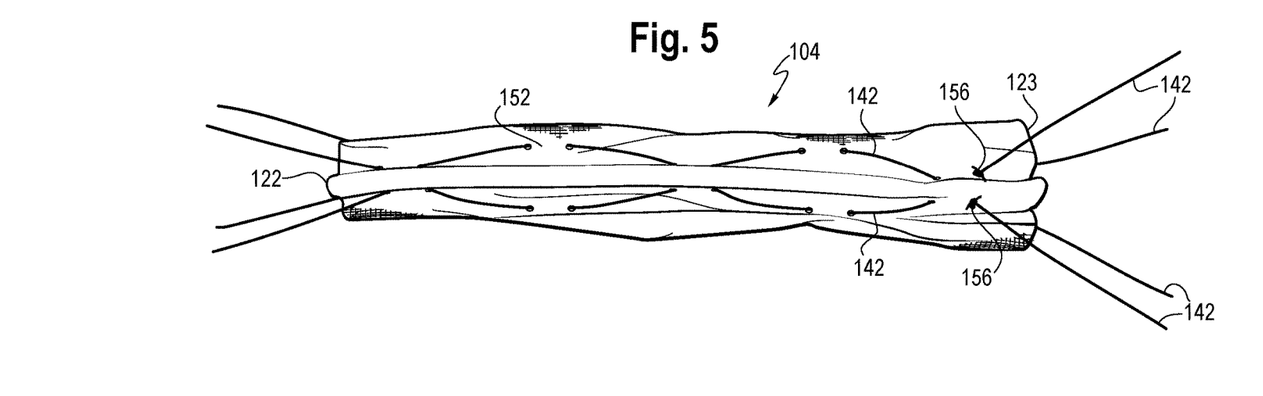
FIG. 5 shows a longitudinal view of one example of a prosthesis illustrated in FIG. 4 with the helical trigger wires in a tensioned configuration.

FIGS. 2 and 5 show a longitudinal side view of an exemplary prosthesis 104 with the helical trigger wires in a tensioned configuration. FIG. 4 shows a longitudinal side view of an exemplary prosthesis 104 with the trigger wires 142 in a relaxed configuration. The inner cannula 108 upon which the prosthesis 104 would be releasably secured is not shown in FIGS. 4 and 5 for purposes of clarity. In addition, the bare proximal fixation stent 128 has also been omitted from FIGS. 4 and 5 for purpose of clarity.

The prosthesis 104 is shown in FIGS. 2 and 5 in a reduced diameter configuration due to the tensioned helical trigger wires 142. It can be seen that four separate helical trigger wires extend both longitudinally and circumferentially from the proximal end 122 to the distal end 123 of the main tubular body 105 in a coiled or helical manner. More or fewer trigger wires 142 may be necessary or desired depending on several factors including, but not limited to the number of proximal or distal apices 130, 132 of the bare proximal fixation stent 128 that are releasably secured to the inner cannula 108. When tension is applied to the helical trigger wires 142, the diameter of the prosthesis 104 is reduced and the proximal fixation stent 128 and/or the graft material 152 is thereby captured down onto the delivery system inner cannula 108. In one example, as the helical trigger wires 142 are pulled distally by the physician to urge the wires 142 into a tensioned configuration, the diameter of the prosthesis 104 and fixation stent 128 is reduced. As shown in FIG. 5, releasable ties or knots 156 are used on the distal end 123 of the main tubular body 105 and/or on the distal end 124 of prosthesis 104 to hold the trigger wires 142 in a taut, tensioned condition and maintain the prosthesis 104 in a reduced diameter state until deployment.

After the prosthesis 104 is delivered to the targeted area in the body vessel, the diameter-reducing arrangement may be relaxed so that the prosthesis 104 and/or fixation stent 128 may be unconstrained and at least partially deployed in a radially outwardly expanded condition as shown in FIG. 1. FIG. 4 shows an exemplary prosthesis 104 with the helical trigger wires 142 in a relaxed configuration. When tension is released from helical trigger wires 142, the graft fabric 152 can relax and the diameter of the prosthesis 104 may be increased. For example, the hemodynamic force or pressure created by the blood flowing through the vessel (and through the lumen 117 of the prosthesis 104) creates sufficient radial outward pressure against the walls of the prosthesis 104 so as to at least partially expand the prosthesis within the vessel.

The diameter-reducing arrangement can be removed by the physician when (s)he no longer requires the diameter to be reduced. The helical trigger wires 142 may be withdrawn by pulling the helical trigger wires 142 distally (either together or one at a time) with sufficient force so that the proximal end 144 of the helical trigger wire(s) 142 is released from the sleeve 140 (and/or released from any other attachment mechanism that may have retained the proximal end 144 of the trigger wire(s) 142). The graft material 152 of the prosthesis 104 exerts negligible radial outward force, thus, the helical trigger wires 142 effectively compress the prosthesis 104 while the force required to withdraw the wires and release and/or at least partially deploy the prosthesis 104 remains acceptably low. Upon release of the helical trigger wires 142, the prosthesis 104 may at least partially expand (full deployment may be prevented for several reasons, including, for example, the proximal fixation stent 128 may still be retained within the introducer tip 112 and/or by the sleeve 140 and/or the prosthesis may still be partially retained by other diameter-reducing mechanisms as described below). As mentioned above, the portions of the prosthesis 104 that are unsupported by a stent exert negligible outward radial force, thus, the hemodynamic force created by the flow of blood through the lumen 117 of the prosthesis 104 serves to at least partially expand the prosthesis 104 within the vessel.

In addition to the trigger wires 142, other diameter-reducing mechanisms may also be utilized, including, for example, diameter-reducing ties may also be used to compress the prosthesis 104 and/or stent subassembly 160 radially inwardly to ensure that a minimized delivery profile is maintained. Diameter-reducing ties may comprise wire (such as nitinol wire), sutures, string, cord or other acceptable material. As shown generally in FIGS. 6-9, diameter-reducing ties can be wrapped circumferentially at least partially or fully around the prosthesis 104 (ties 182 in FIGS. 7-9) and/or around the stent subassembly 160 (ties 184 in FIG. 6) to radially fix and retain the respective elements to the inner cannula 108. Some suitable diameter reducing tie mechanisms are shown and described in U.S. Publication No. 2007-0043425 A1 to Roeder et al., which disclosure is incorporated by reference herein in its entirety.

The diameter-reducing ties 182, 184 may include sutures that are wrapped around the graft material 152 of the prosthesis 104 and/or around the stent subassembly 160 at one or more pre-selected positions, woven or stitched directly through the graft material 152 or woven through one or more of the stent segments of the stent subassembly 160 or simply wound or positioned around the prosthesis 104 or stent subassembly 160 to allow unraveling or unwrapping of the diameter-reducing ties 182, 184 during deployment.

Figure 7:
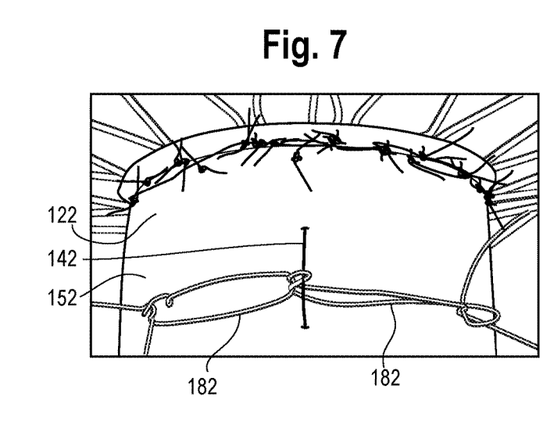
FIG. 7 illustrates one example of a diameter-reducing tie for a prosthesis in an expanded configuration.
Figure 8:
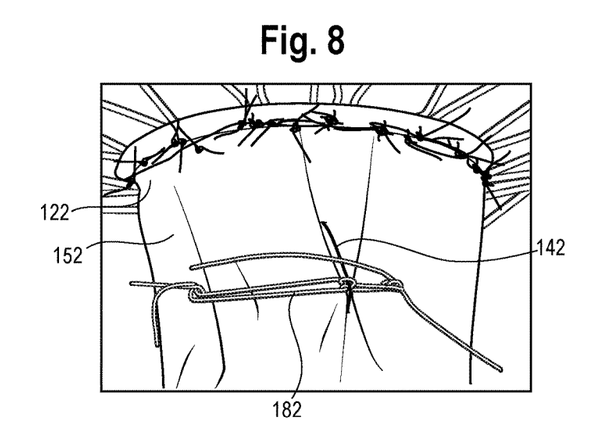
FIG. 8 illustrates the diameter-reducing tie of FIG. 7 in a partially tensioned configuration.
Figure 9:
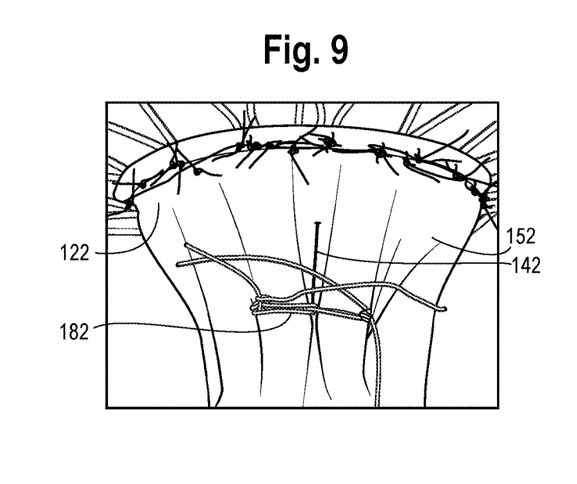
FIG. 9 illustrates the diameter-reducing tie of FIG. 7 in a tensioned condition.

As shown in FIG. 6, a series of 5 diameter-reducing ties 184 are used to radially inwardly compress the stent subassembly 160 to the inner cannula 108 (although more or fewer diameter-reducing ties 184 may be utilized depending on the length, configuration and/or shape of the stent subassembly 160). Diameter-reducing ties 182 may also be used to secure the bare fixation stent 128 extending from the proximal end 122 of the prosthesis 104 and/or the graft material 152 in a radially inwardly compressed delivery configuration on the inner cannula 108. As shown in FIGS. 7-9, a diameter-reducing tie 182 may be circumferentially woven or stitched around or through the graft material 152 (FIG. 7) and tightened (FIGS. 8 and 9) to radially inwardly constrain the graft material 152 against the inner cannula 108.

Additional ties 182 may also be used to radially inwardly constrain one or more of the proximal or distal apices 130, 132 of the bare fixation stent 128 to ensure that the fixation stent 128 is radially inwardly compressed and maintains a low delivery profile, while also providing independent release capability during deployment. One or more trigger wires 142 may be used to hold the diameter-reducing ties in a radially inwardly constrained delivery configuration (FIG. 9).

At least one of the helical trigger wire(s) 142 may be used to hold any one or more of the diameter-reducing ties 182, 184 taut, thereby retaining the compressed element in the compressed condition on the inner cannula 108. One or more trigger wires 142 may be used to maintain the diameter-reducing mechanisms used on the prosthesis 104 in a compressed condition and a separate series of trigger wires 142 may be used to maintain the diameter-reducing mechanisms used on the stent subassembly 160 in a compressed condition. Alternatively, the same set of helical trigger wires 142 may be used to maintain the diameter-reducing mechanisms on both the prosthesis 104 and stent subassembly 160 in a compressed condition. Removal of one or more of the trigger wires 142 may facilitates release of the diameter-reducing ties 182, 184, or, alternatively, the diameter-reducing ties 182, 184 may be released and removed separately from the trigger wires 142.

Alternatively or in combination with the above-mentioned diameter-reducing mechanisms, a retractable sheath (not shown) that is disposed about the prosthesis 104 and/or about the stent subassembly 160 may be used to hold the respective components in a reduced diameter delivery configuration on the introducer 102. Thus, in order to fully release the prosthesis 104 from the introducer 102 during deployment, any one or more of these additional diameter-reducing mechanisms, including but not limited to the helical trigger wires(s) 142, diameter-reducing ties 182, 184, sheath, etc., must be removed and released before the prosthesis 104 and/or the stent subassembly 160 can be fully released from the introducer 102 and deployed within the vessel. Introducers suitable for use with the present invention include those shown and described in U.S. Pat. No. 8,876,879 to Hartley et al., in particular FIGS. 1-6 and the accompanying text, which patent is incorporated by reference herein in its entirety; U.S. Pat. No. 8,740,964 to Hartley et al., in particular FIGS. 1-8 and the accompanying text, which patent is incorporated by reference herein in its entirety; U.S. Pat. No. 8,911,488 to Hartley et al., in particular FIGS. 2-3 and the accompanying text, which patent is incorporated by reference herein in its entirety, and U.S. Pat. No. 9,173,756 to Hopkins et al., its figures and accompanying text, which patent is incorporated by reference herein in its entirety After the prosthesis 104 has been at least partially deployed, the introducer 102 can be further manipulated in order to position and deploy the stent subassembly 160 within the lumen 117 of the prosthesis 104. Alternatively, if the stent subassembly 160 has been loaded on a separate introducer than the one used to deliver the prosthesis 104, then this separate introducer can be tracked to a desired location within the vessel to thereby position the stent subassembly 160 within the lumen 117 of the prosthesis 104 for deployment therein.

Loading the prosthesis 104 and the stent subassembly 160 onto different portions of a deliver) device 100 (or on separate delivery devices) while utilizing low profile or ultra low profile graft material 152 and a low profile stent subassembly 160 configuration releasably secured to the introducer 102 by one or more helically wound trigger wires 142, the entire graft load volume and overall delivery profile of the device 100 can be minimized.

While various embodiments of the invention have been described, the invention is not to be restricted except in light of the attached claims and their equivalents.

We claim:

1. A delivery device system for delivering a low profile prosthesis to a body vessel comprising:
    an inner cannula having a proximal end and a distal end;
    a prosthesis formed of biocompatible graft material and having a proximal end and a distal end, the prosthesis disposed about the proximal end of the inner cannula, wherein the prosthesis comprises a first configuration in which the prosthesis is releasably secured to the inner cannula in a radially inwardly contracted low profile delivery configuration and a second configuration in which the prosthesis is at least partially radially outwardly expanded;
    a first trigger wire having a tensioned condition and a relaxed condition and extending longitudinally and circumferentially about the prosthesis in only a helical configuration from the proximal end of the prosthesis to the distal end of the prosthesis;
    a second trigger wire, separate from the first trigger wire, having a tensioned condition and a relaxed condition and extending longitudinally and circumferentially about the prosthesis in only a helical configuration from the proximal end of the prosthesis to the distal end of the prosthesis;
    wherein when the first and second helical trigger wires are in the tensioned condition, the prosthesis is releasably secured to the inner cannula in the radially inwardly contracted low profile delivery configuration,
    wherein prosthesis comprises a plurality of sets of four holes extending longitudinally along the length of the prosthesis and each of the first and second helical trigger wires extends through two of the four holes of each set of four holes, such that the first and second helical trigger wires are woven in and out of the graft material as they extend from the proximal end to the distal end of the prosthesis.

2. The system of claim 1, wherein at least one of the first and second helical trigger wires is releasably secured to the graft material by one or more sutures.

3. The system of claim 1, wherein the first trigger wire is helically-wound in a clockwise direction and wherein the second trigger wire is helically-wound in a counter-clockwise direction.

4. The system of claim 1, further comprising a bare stent extending from an end of the prosthesis.

5. The system of claim 4 wherein the bare stent comprises a series of proximal apices and a series of distal apices.

6. The system of claim 5, wherein the series of distal apices of the bare stent are secured to the proximal end of the prosthesis.

7. The system of claim 6, wherein the first trigger wire releasably holds at least one of the proximal stent apices of the bare stent to the inner cannula when the first trigger wire is in the tensioned condition.

8. The system of claim 7, wherein the first trigger wire further releasably holds at least one of the distal stent apices of the bare stent to the inner cannula when the first trigger wire is in the tensioned condition.

9. The system of claim 4 wherein a proximal end of the first trigger wire is releasably secured to the proximal end of the inner cannula, loops over at least one proximal stent apex and over at least one distal stent apex and extends longitudinally and circumferentially about the prosthesis in the helical configuration from the proximal end of the prosthesis to the distal end of the prosthesis.

10. The system of claim 9 wherein a proximal end of the second trigger wire is releasably secured to the proximal end of the inner cannula, loops over at least one proximal stent apex and over at least one distal stent apex and extends longitudinally and circumferentially about the prosthesis in a helical configuration from the proximal end of the prosthesis to the distal end of the prosthesis.

11. The system of claim 1 further comprising a third trigger wire, separate from the first and second trigger wires, having a tensioned condition and a relaxed condition and extending longitudinally and circumferentially about the prosthesis in only a helical configuration from the proximal end of the prosthesis to the distal end of the prosthesis.

12. The system of claim 1 further comprising at least one diameter-reducing tie wrapped circumferentially around at least part of the prosthesis.

13. The system of claim 1 wherein the inner cannula comprises at least one of a single lumen cannula, multiple lumen cannula or a combination of a single lumen cannula and multiple lumen cannula.

14. The system of claim 1 further comprising a stent subassembly releasably secured to the inner cannula longitudinally distal to the prosthesis such that there is no overlap between the prosthesis and the stent subassembly.

15. The system of claim 1 wherein the prosthesis is substantially unstented.

16. A low profile prosthesis delivery system, the system comprising:
 at least one introducer comprising an inner cannula having a proximal end and a distal end;
 a prosthesis formed of biocompatible graft material and having a proximal end and a distal end, and a lumen therebetween, and is substantially unsupported along its length;
 wherein the prosthesis is disposed about the proximal end of the inner cannula, wherein the prosthesis comprises a first configuration in which the prosthesis is releasably secured to the inner cannula in a radially inwardly contracted low profile delivery configuration and a second configuration in which the prosthesis is at least partially radially outwardly deployed;
 a first trigger wire having tensioned condition and a relaxed condition and extending longitudinally and circumferentially about the prosthesis in only a helical configuration from the proximal end of the prosthesis to the distal end of the prosthesis;
 a second trigger wire, separate from the first trigger wire, having tensioned condition and a relaxed condition and extending longitudinally and circumferentially about the prosthesis in only a helical configuration from the proximal end of the prosthesis to the distal end of the prosthesis;
 wherein when the first and second helical trigger wires are in the tensioned condition, the prosthesis is releasably secured to the inner cannula in the radially inwardly contracted low profile delivery configuration; and
 a stent subassembly separate from the prosthesis comprising one or more stents,
 wherein the first and second helical trigger wires are woven in and out of the graft material as they extend from the proximal end to the distal end of the prosthesis and cross over each other at a plurality of points along the length of the graft within the lumen.

17. The system of claim 16, wherein the prosthesis and stent subassembly are loaded onto separate sections of a single introducer so that there is no overlap between the prosthesis and stent subassembly as loaded.

18. A method for releasably retaining a prosthesis to a delivery cannula, the delivery cannula having a proximal end and a distal end and a prosthesis releasably secured to the proximal end of the delivery cannula, the prosthesis comprising a biocompatible graft material having a proximal end and a distal end, wherein the prosthesis comprises a first configuration in which the prosthesis is releasably secured to the delivery cannula in a radially inwardly contracted low profile delivery configuration and a second configuration in which the prosthesis is at least partially radially outwardly deployed, the method comprising:
 (a) extending a first trigger wire having a tensioned condition and a relaxed condition longitudinally and circumferentially about the prosthesis in only a helical configuration from the proximal end of the prosthesis to the distal end of the prosthesis, wherein the first trigger wire is helically wound;
 (b) extending a second trigger wire, separate from the first trigger wire, having a tensioned condition and a relaxed condition longitudinally and circumferentially about the prosthesis in only a helical configuration from the proximal end of the prosthesis to the distal end of the prosthesis, wherein the second trigger wire is helically wound;
 (c) tensioning the first and second helical trigger wires to releasably secure the prosthesis in a radially inwardly contracted low profile delivery configuration to the delivery cannula,
 wherein each of the first and second trigger wires cross over each other within an internal lumen of the prosthesis.

19. The method of claim 18 wherein the prosthesis further comprises a bare proximal fixation stent extending proximally from the proximal end of the graft material, the proximal fixation stent having a series of proximal apices and a series of distal apices, the method further comprising:

releasably securing a proximal end of the first trigger wire to the proximal end of the delivery cannula, looping the first trigger wire over at least one proximal stent apex and looping the first trigger wire over at least one distal stent apex to releasably secure at least a portion of the proximal fixation stent to the delivery cannula in a radially inwardly contracted low profile delivery configuration when the first trigger wire is in the tensioned condition, and releasably securing a proximal end of the second trigger wire to the proximal end of the delivery cannula, looping the second trigger wire over at least one proximal stent apex and looping the second trigger wire over at least one distal stent apex to releasably secure at least a portion of the proximal fixation stent to the delivery cannula in a radially inwardly contracted low profile delivery configuration when the second trigger wire is in the tensioned condition.

* * * * *